US005395750A

United States Patent [19]

Dillon et al.

[11] Patent Number: 5,395,750

[45] Date of Patent: Mar. 7, 1995

[54] METHODS FOR PRODUCING PROTEINS WHICH BIND TO PREDETERMINED ANTIGENS

[75] Inventors: Patrick J. Dillon, Bloomfield; Craig A. Rosen, Glen Ridge, both of N.J.

[73] Assignee: Hoffmann-La Roche Inc., Nutley, N.J.

[21] Appl. No.: 843,125

[22] Filed: Feb. 28, 1992

[51] Int. Cl.$^6$ ...................... C07H 19/00; C12P 21/06; C12N 15/00; C12N 1/20

[52] U.S. Cl. ...................................... 435/5; 435/71.1; 435/240.27; 435/320.1; 435/252.3; 435/69.1; 536/23.53

[58] Field of Search ................... 435/71.1, 69.7, 320.1, 435/240.27, 5, 252.3, 69.1; 536/28.53

[56] References Cited

U.S. PATENT DOCUMENTS 5,223,409 6/1993 Ladner et al. ...................... 435/69.7

FOREIGN PATENT DOCUMENTS

91/13909 9/1991 WIPO .
91/19739 12/1991 WIPO .
92/02551 2/1992 WIPO .

OTHER PUBLICATIONS

McCafferty et al., Nature 348:552–554 (1990).
Huse et al., Science 246:1275–1281 (1989).
Clackson et al., Nature 352:624–628 (1991).
Dillon and Rosen, BioTechniques vol. 9, pp. 298 and 300 (1990).
Fuchs et al., Bio/Technology 9:1369–1372 (1991).
Barbas III et al., Proc. Natl. Acad. Sci. USA 88:7978–7982 (1991).
Winter and Milstein, Nature 349:293–299 (1991).
Bird et al., Science 243:423–426 (Oct. 31, 1988).

*Primary Examiner*—David L. Lacey
*Assistant Examiner*—Donald E. Adams
*Attorney, Agent, or Firm*—George M. Gould; William H. Epstein; Catherine R. Roseman

[57] ABSTRACT

Methods of producing a protein capable of binding to a predetermined antigen, screening libraries containing such proteins, and proteins and synthetic genes containing randomized sequences are disclosed.

8 Claims, 16 Drawing Sheets

VARIABLE HEAVY REGION
E V Q L V E S G G G L V Q P G G S L R L S
C A A S G F T F S [X X X X] W V R Q A P G
K G L E W V A [X X X X X X X X X X X X X
X X X] R F T I S R D D S K N T L Y L Q M N
S L R A E D T A V Y Y C A R [X X X X X X
X X X X X] W G Q G T L V T V S S

LINKER REGION
[G G G G S G G G G S G G G G S]

VARIABLE LIGHT REGION
D I Q M T Q S P S S L S A S V G D R V T I
T C [X X X X X X X X X X X] W Y Q Q K P G K
A P K L L I Y [X X X X X X X] G V P S R F S
G S G S G T D F T L T I S S L Q P E D F A
T Y Y C [X X X X X X X X X] F G Q G T K V E
I K R T

FIG. 2

| | | | | | |
|---|---|---|---|---|---|
| 1 | gaagttcaac | tggttgaatc | cggtggtggt | ctggttcaac | caggtggttc |
| 51 | cctgcgtctg | tcctgtgctg | cttccggttt | caccttctcc | nnnnnnnnnn |
| 101 | nnnnntgggt | tcgtcaagct | ccaggtaaag | gtctggaatg | ggttgctnnn |
| 151 | nnnnnnnnnn | nnnnnnnnnn | nnnnnnnnnn | nnnnnnnnnn | nnnnnnnncg |
| 201 | tttcaccatc | tcccgtgacg | actccaaaaa | caccctgtac | ctgcaaatga |
| 251 | actccctgcg | tgctgaagac | accgctgttt | actactgtgc | tcgtnnnnnn |
| 301 | nnnnnnnnnn | nnnnnnnnnn | nnnnnnnnnn | nnntggggtc | aaggtaccct |
| 351 | ggttaccgtt | tcctccggtg | gtggtggttc | cggtggtggt | ggttctggtg |
| 401 | gtggtggttc | cgacatccaa | atgacccaat | ccccatcctc | tctgtccgct |
| 451 | tccgttggtg | accgtgttac | catcacctgt | nnnnnnnnnn | nnnnnnnnnn |
| 501 | nnnnnnnnnn | nnntggtacc | aacaaaaacc | aggtaaagct | ccaaaactgc |
| 551 | tgatctacnn | nnnnnnnnnn | nnnnnnnnng | gtgttccatc | ccgtttctcc |
| 601 | ggttccggtt | ctggtaccga | cttcaccctg | accatctcct | ctctgcaacc |
| 651 | agaagacttc | gctacctact | actgtnnnnn | nnnnnnnnnn | nnnnnnnnnn |
| 701 | nnttcggtca | aggtaccaaa | gttgaaatca | aacgtacc | |

FIG. 3

| | | | | | |
|---|---|---|---|---|---|
| 1 | gaagttcaac | tggttgaatc | cggtggtggt | ctggttcaac | caggtggttc |
| 51 | cctgcgtctg | tcctgtgctg | cttccggttt | caccttctcc | nnnnnnnnnn |
| 101 | nnnnntgggt | tcgtcaagct | ccagg | | |
| | | | | | |
| 1 | ggagtcgtca | cgggagatgg | tgaaacgnnn | nnnnnnnnnn | nnnnnnnnnn |
| 51 | nnnnnnnnnn | nnnnnnnnnn | nnnnnnnnag | caacccattc | cagaccttta |
| 101 | cctggagctt | gacgaaccca | | | |
| | | | | | |
| 1 | cgtttcacca | tctcccgtga | cgactccaaa | aacaccctgt | acctgcaaat |
| 51 | gaactccctg | cgtgctgaag | acaccgctgt | ttactactgt | gctcgt |
| | | | | | |
| | caccggagga | aacggtaacc | agggtacctt | gaccccannn | nnnnnnnnnn |
| 51 | nnnnnnnnnn | nnnnnnnnnn | nnnnnnacga | gcacagtagt | aaacagcggt |
| 101 | g | | | | |

FIG. 4A

```
    tggttaccgt  ttcctccggt  ggtggtggtt  ccggtggtgg  tggttctggt
51  ggtggtggtt  ccgacatcca  aatgacccaa  tccccatcct  ctctgtccgc
101 ttccgttggt  gaccgtgtta  ccatca

    gatcagcagt  tttggagctt  tacctggttt  ttgttggtac  cannnnnnnn
51  nnnnnnnnnn  nnnnnnnnnn  nnnnnacagg  tgatggtaac  acggtcacca
101 acggaa

    ggtacgtttg  atttcaactt  tggtaccttg  accgaannnn  nnnnnnnnnn
51  nnnnnnnnnn  nnnacagtag  taggtagcga  agtcttctgg  ttgcagagag
101 gagatggtca  gggtgaagt

    caggtaaagc  tccaaaactg  ctgatctacn  nnnnnnnnnn  nnnnnnnnnn
51  ggtgttccat  cccgtttctc  cggttccggt  tctggtaccg  acttcaccct
101 gaccatctcc  tctctg
```

FIG. 4B

A. SINGLE CHAIN ANTIBODY (FV)
VARIABLE HEAVY  LINKER  VARIABLE LIGHT

☐ FRAMEWORK REGION   ▨ HYPERVARIABLE REGION

B. PRIMER DESIGN

OVERLAPPING OLIGONUCLEOTIDES FIG.5B

C. FIRST PCR REACTION
CYCLE 1

CYCLE 2

CYCLE 3

CYCLE 4

D. SECOND PCR REACTION

5. FLANKING PRIMER

FULL LENGTH SYNTHETIC Fv DNA SEQUENCE

3 FLANKING PRIMER

PJD1 STRAIN
MC1061+pDM1.1+FUSE 2

PJD2 STRAIN
MC1061+FUSE 2

PHAGE ANTIBODY LIBRARY lam B ANTIBODY FUSION LIBRARY

PHAGE ANTIBODY LIBRARY

PHAGEMID ANTIBODY LIBRARY

1. PHAGE/BACTERIA EXPRESSING SYNTHETIC Fv FRAGMENTS WILL BE INCUBATED WITH IMMOBILIZED ANTIGEN.

2. UNBOUND AND NON-SPECIFIC PHAGE/ BACTERIA WILL BE WASHED FROM ANTIGEN

3. BOUND PHAGE/BACTERIA WILL BE ELUTED FROM THE ANTIGEN AND WILL BE ENRICHED THROUGH SEQUENTIAL ROUNDS OF SCREENING

```
1    EVQLVESGRGLVQPGGSLRLSCAASGFTFSHFLVAWVRQAPGKGLEWVAT  50
1    EVQLVESGGGLVQPGGSLRLSCAASGFTFSXXXXXWVRQAPGKGLEWVAX  50

51   YSMISRARVLDGSSFNGRYTISRDDSKNTLYLQMNSLRAEDTAVYYCARIG  100
51   XXXXXXXXXXXXXXXXXRFTISRDDSKNTLYLQMNSLRAEDTAVYYCARXX  100

101  STHTIPRLSQYGGQGTLVTVSSGGGGSGGGGSGGGGSDIQMTQSPSSLSA  150
101  XXXXXXXXXXXWGQGTLVTVSSGGGGSGGGGSGGGGSDIQMTQSPSSLSA  150

151  SVGDRVTITCKLRGPQPHAITWYQQKPGKAPKLLIYYDGQTLVGVPSRFS  200
151  SVGDRVTITCXXXXXXXXXXXWYQQKPGKAPKLLIYXXXXXXXGVPSRFS  200

201  GSGSGTDFTPTISSLEPEDFATYYCTPTHKIDSPFGQGTKVEIKRT  246
201  GSGSGTDFTLTISSLQPEDFATYYCXXXXXXXXXFGQGTKVEIKRT  246
```

FIG. 13

```
91   GAAGTTCAACTGGTTGAATCCGGTCGTGGTCTGGTTCAACCAGGTGGTTC  140
1    gaagttcaactggttgaatccggtggtggtctggttcaaccaggtggttc  50

141  CCTGCGTCTGTCCTGTGCTGCTTCCGGTTTCACCTTCTCCCATTTTTTGG  190
51   cctgcgtctgtcctgtgctgcttccggtttcaccttctccnnnnnnnnnn  100

191  TGGCGTGGGTTCGTCAAGCTCCAGGTAAAGGTCTGGAATGGGTTGCTACC  240
101  nnnnntgggttcgtcaagctccaggtaaaggtctggaatgggttgctnnn  150

241  TACTCAATGATTAGCCGGGCCCGaGTACTCGATGGCTCCTTTAATGGACG  290
151  nnnnnnnnnnnnnnnnnnnnnnnnnnnnnnnnnnnnnnnnnnnnnnnncg  200

291  TTaCACCATCTCCCGTGACGACTCCAAAAACACCCtgTACCtgcaaatga  340
201  tttcaccatctcccgtgacgactccaaaaacaccctgtacctgcaaatga  250

341  actccctgcgtgctgaagaCACCGCTGtTTACTACTGTGCTCGTATTGGT  390
251  actccctgcgtgctgaagacaccgctgtttactactgtgctcgtnnnnnn  300

391  TCTACGCACACAATCCCACGACTGTCTCAATACGGGGgTCAAGGTACCCT  440
301  nnnnnnnnnnnnnnnnnnnnnnnnnnnnnnnnntggggtcaaggtaccct  350
```

FIG. 14A

```
441 GGTTaccgtttcctccggtggtggtggttccggtggtgGTGGTTCTGGTG 490
351 ggttaccgtttcctccggtggtggtggttccggtggtggtggttctggtg 400

491 GTGGTGGTTCCGACATCCAAATGACCCAATCCCCATCCTCTCTGTCCGCT 540
401 gtggtggttccgacatccaaatgacccaatccccatcctctctgtccgct 450

541 TCCGTTGGTGACCGTGTTACCATCACCTGTAAACTCAGAGGACCACAACC 590
451 tccgttggtgaccgtgttaccatcacctgtnnnnnnnnnnnnnnnnnnnn 500

591 ACACGCCATTACATGGTACCAACAAAAACCAGGTAAAGCTCCAAAACTGC 640
501 nnnnnnnnnnnnnntggtaccaacaaaaaccaggtaaagctccaaaactgc 550

641 TGATctaCTACGACGGCCAAACGTTGGTGGGTGTTCCATCCCGTTTCTCC 690
551 tgatctacnnnnnnnnnnnnnnnnnnnnnnggtgttccatcccgtttctcc 600

691 GGTTCTGGTTCTGGTACCGACTTCACCCCGACCATCTCCTCTCTGGAACC 740
601 ggttccggttctggtaccgacttcaccctgaccatctcctctctgcaacc 650

741 AGAAGACTTCGCTACCTACTACTGTACTCCTACGCACAAGATCGATAGCC 790
651 agaagacttcgctacctactactgtnnnnnnnnnnnnnnnnnnnnnnnnn 700

791 CATTCGGTCAAGGTACCAAAGTTGaAaTCAAACGTACC 828
701 nnttcggtcaaggtaccaaagttgaaatcaaacgtacc 738
```

FIG. 14B

METHODS FOR PRODUCING PROTEINS WHICH BIND TO PREDETERMINED ANTIGENS

BACKGROUND OF THE INVENTION

The very selective and specific binding characteristics of antibodies makes these molecules extremely attractive for use in a variety of medical and basic research applications. Traditional methods for generating antibodies involve immunization and hybridoma technology for the generation of monoclonal antibodies. Recently, PCR based techniques have made it possible to engineer humanized antibodies which may serve as better therapeutic agents than their murine counterparts (Winter, and Milstein, 1991; Co, and Queen, 1991; Orlandi et al. 1989). Furthermore, this technology has progressed to the point where it is now possible to clone the immunoglobulin (antibody) repertoire of an immunized mouse from spleen cells into phage expression vectors and identify expressed antibody fragments specific to the antigen used for immunization (Winter, and Milstein, 1991; Gussow et al. 1989; Hodgson, 1991; Marks et al. 1991; Garrard et al. 1991; Duschosal et al. 1992; Kang et al. 1991b; Clackson et al. 1991; Huse et al. 1989; Persson et al. 1991; Kang et al. 1991a; Hoogenboom et al. 1991; Barbas III et al. 1991). However, this technology has had little success in identifying specific antigen binding antibody fragments from unimmunized animals suggesting that there may be a prerequisite for prior immunization to the antigen of interest.

SUMMARY OF THE INVENTION

The claimed invention provides a method for producing a protein which binds to an antigen of choice, by using the antigen to screen a library of proteins which have been generated by using DNA synthesis and recombinant techniques combined with randomizing methods. The proteins, also referred to as synthetic antibodies, have the structure of antibodies, specifically Fab or Fv fragments, and contain randomized binding sequences which may correspond in length to hypervariable regions (CDRs).

The techniques of this invention provide a method to generate a library of completely de novo synthesized antibody fragments which allows the bypass of both immunization and the necessity to use animals. The development of a synthetic antibody library has many advantages over other antibody libraries which are derived from immunized or unimmunized animals. The synthetic antibodies are developed without the use of animals (or hybridoma technology) and the problems associated with tolerance can be avoided. In addition, the synthetic antibody approach can be used for identifying antibodies against molecules which appear to be non-immunogenic or fail to induce immune response in animals. Furthermore, synthetic antibodies can be used to fill possible "holes" which may be present in an animals immune system repertoire.

The structure of an immunoglobulin consists of heavy and light chains which can be further defined into variable and constant domains which are indicated above. The smallest antibody fragment which forms an antigen binding site is referred to as an Fv fragment. Genetic engineering techniques have made it possible to generate single chain antibody (Fv) fragments. These Fv fragments consist of the heavy and light chain variable regions tethered together by a flexible glycine-serine linker. The variable regions can be further subdivided into framework regions which are fairly conserved among antibodies and hypervariable regions (CDR) which are quite diverse and are important in defining antigen specificity.

There are many uses for such synthetic antibodies and libraries. Some exemplary uses are listed below.

Synthetic antibody libraries can be used to complement other types of antibody libraries derived from animals in any drug screening or other ligand screening procedures.

Synthetic antibody libraries can be manipulated and modified for use in combinatorial type approaches in which the heavy and light chain variable regions are shuffled and exchanged between synthetic antibodies in order to affect specificities and affinities. This enables the production of antibodies which bind to a selected antigen with a selected affinity. For example, catalytic antibodies (abzymes) could be constructed. Antibodies with enhanced affinities can also be produced.

The approach of constructing synthetic single chain antibodies is directly applicable to constructing synthetic Fab fragments which can also be easily displayed and screened in the same manner.

The diversity of the synthetic antibody libraries can be increased by altering the chain lengths of the CDRs and also by incorporating changes in the framework regions which may affect antibody affinity. In addition, alternative libraries can be generated with varying degrees of randomness or diversity by limiting the amount of degeneracy at certain positions within the CDRs. The synthetic library can be modified further by varying the chain lengths of the CDRs and adjusting amino acids at defined position in the CDRs or the framework region which may affect affinities. Antibodies identified from the synthetic antibody library can easily be manipulated to adjust their affinity and or effector functions. In addition, the synthetic antibody library is amenable to use in combinatorial type approaches used by others. This may result in the increasing of the affinities of the synthetic antibodies during the screening procedures.

The synthetic antibody library can be used for the generation and identification of anti-idiotypic antibodies which may mimic ligand and/or receptor molecules, and CDRs from screened synthetic antibodies can be used as potential peptidomimetics.

Screening of the synthetic antibody library can be modified to identify synthetic antibodies which may interact with their ligand under certain defined conditions (i.e., under reducing conditions which may be present in the intracellular environment.)

The strategy of constructing de novo synthetic antibodies can be adapted to the development of peptide libraries which are conformational in nature.

Synthetic antibodies identified from screening can be used for diagnostics such as the identification of any disease marker. Also, synthetic antibodies identified from screening can be used for the development of immunotherapeutics such as antibodies which can be administered for passive immunization or immunoconjugates which may be used to target tumors or other targets.

The coding sequences for identified synthetic antibodies can be manipulated using state of the art cloning strategies so that their antigen binding specificity can be grafted onto any immunoglobulin class or subtype.

The synthetic antibody library can be used for the screening of minute amounts of antigen which may not be available in sufficient quantity for the immunization of an animal.

The synthetic antibodies can be expressed to high levels in both prokaryotes and eukaryotes using present available technologies.

The synthetic antibodies can be used in any and all applications in which antibodies derived from other sources or by other means are used.

1A. Structure of full antibody

1B. Structure of single-chain antibody (Fv)

FIG. 2. Amino acid [SEQ ID:1] sequence of synthetic Fv. Hypervariable region residues are replaced with X to represent any of the 20 amino acids.

FIG. 3. Nucleotide sequence encoding synthetic Fv of FIG. 2. n represents any nucleotide. Codon usage is biassed for expression in *E. coli* and *S. cerevisiae*. [SEQ ID:2]

FIGS. 4A–4B. Oligonucleotides synthesized for use in generation of synthetic gene templates. [SEQ ID:3], [SEQ ID:4], [SEQ ID:5], [SEQ ID:6], [SEQ ID:7], [SEQ ID:8], [SEQ ID:9], [SEQ ID:10]

FIGS. 5A–5D. Diagram of PCR production of synthetic gene encoding Fv 5A: Single chain antibody (Fv), 5B: Primer design, 5C: First PCR reaction, 5D: Second PCR reaction.

Figure 6:
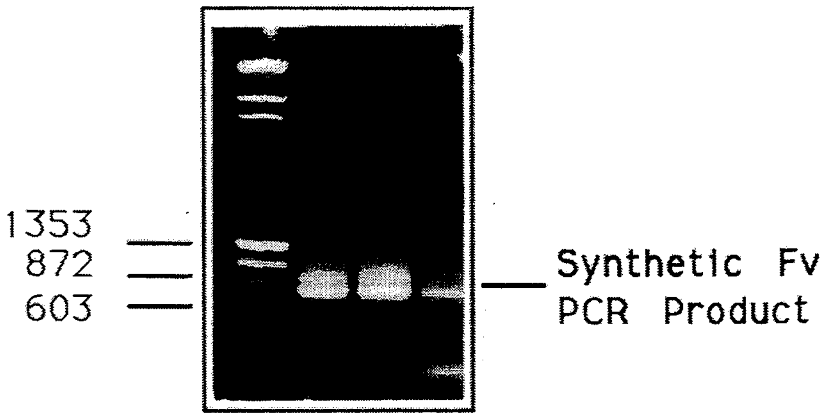

FIG. 6. Ethidium bromide stained agarose gel showing synthetic gene product of second PCR step.

Figure 7:
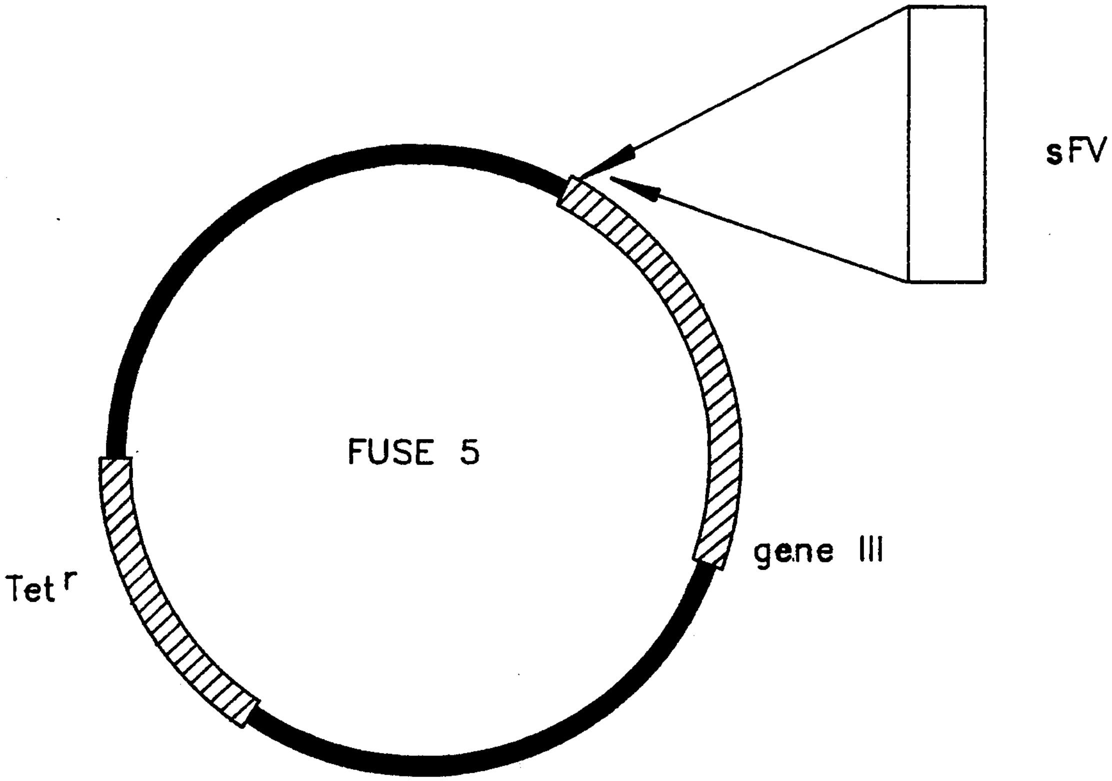

FIG. 7. Diagram of FUSE 5 phage display vector.

Figure 8:
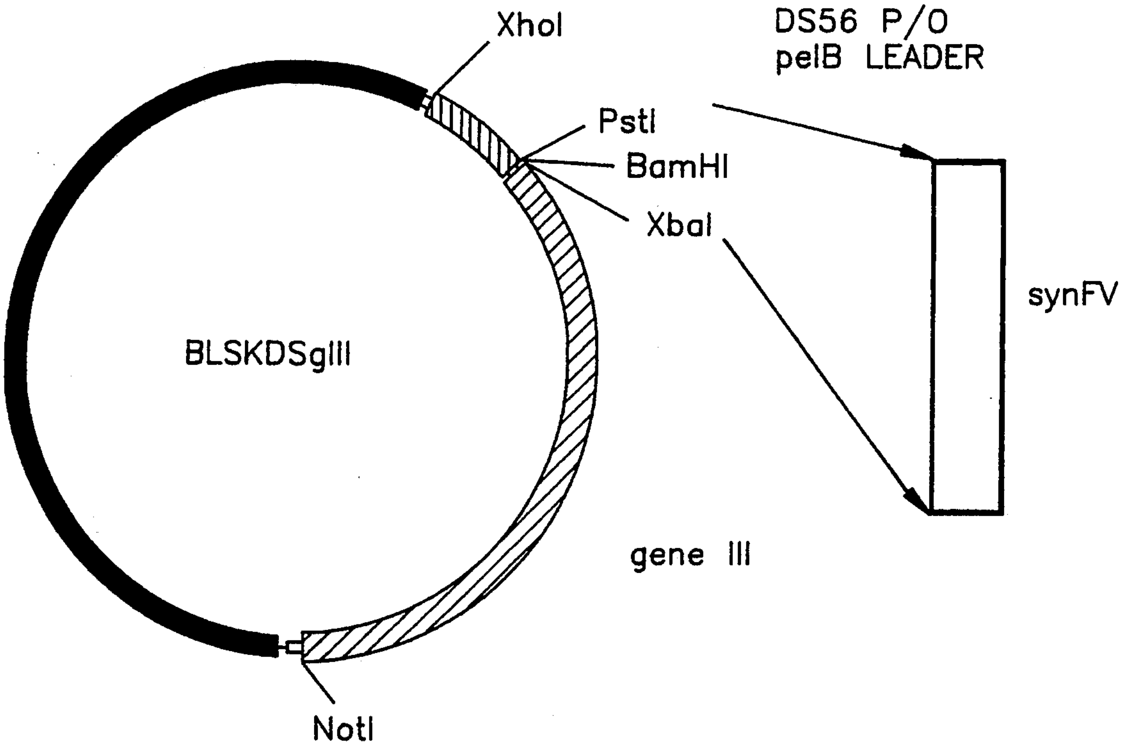

FIG. 8. Diagram of Gene III phagemid vector.

Figure 9A:
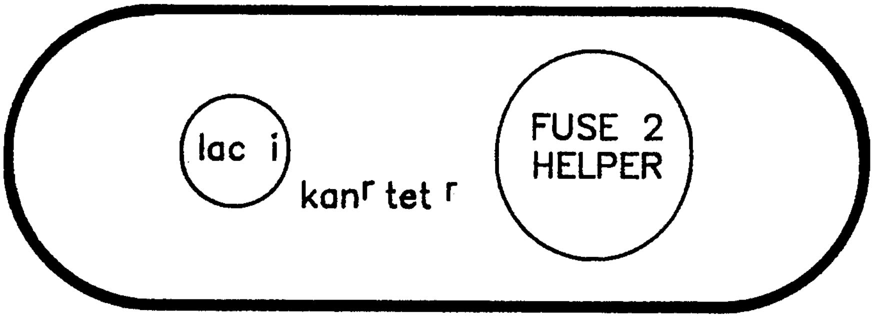
Figure 9B:
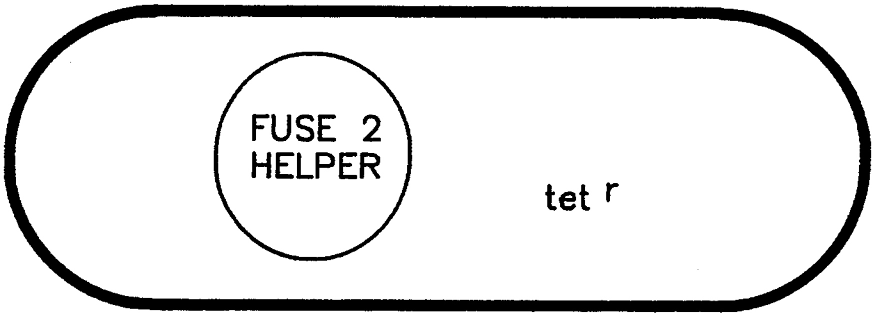

FIG. 9. Diagram of helper phage *E. coli* strains. 9A: PJD1 strain, 9B: PJD2 strain.

Figure 10:
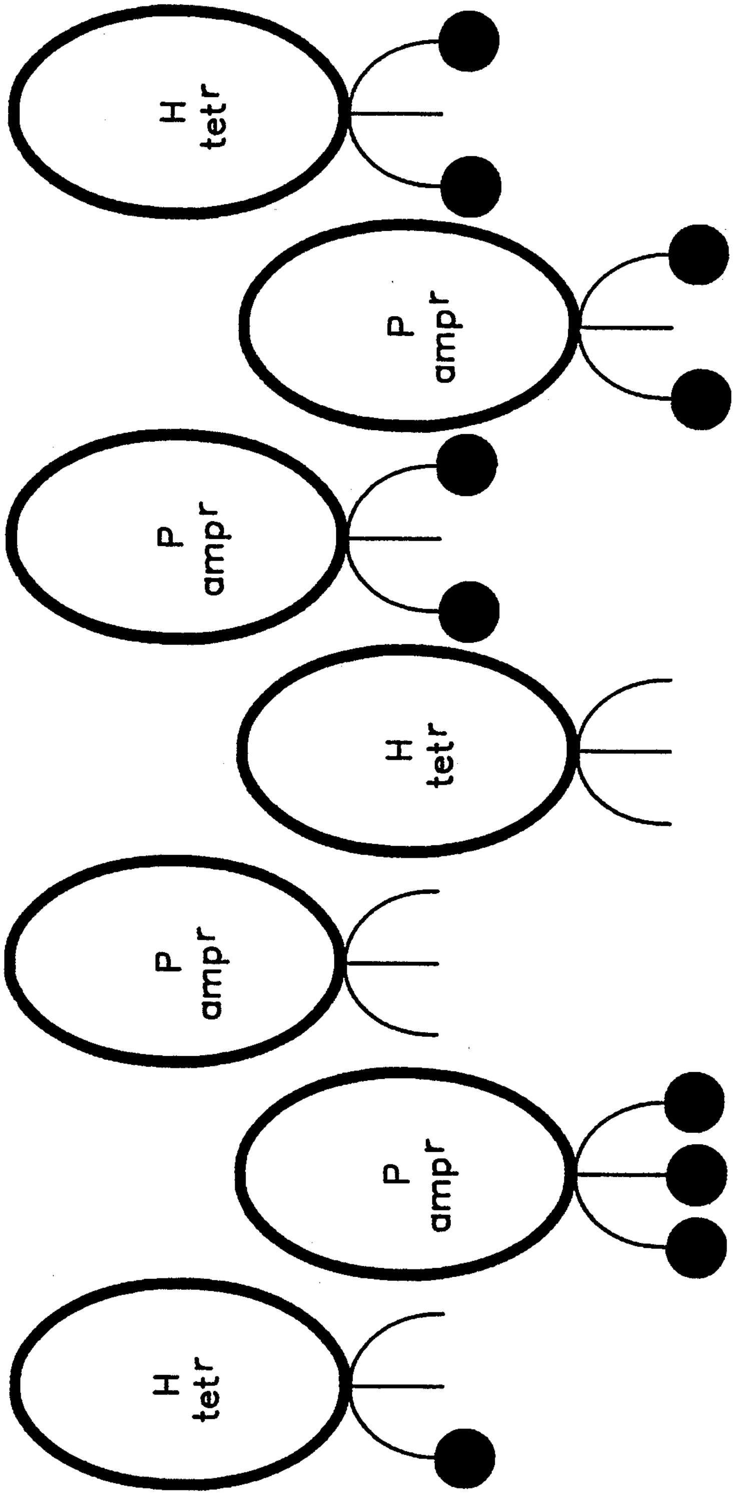
Figure 11A:
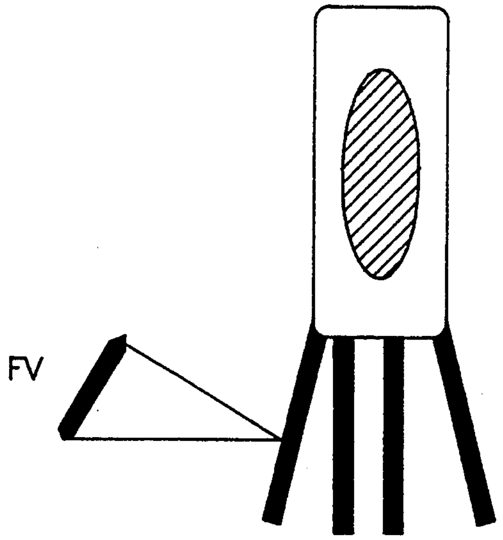
Figure 11B:
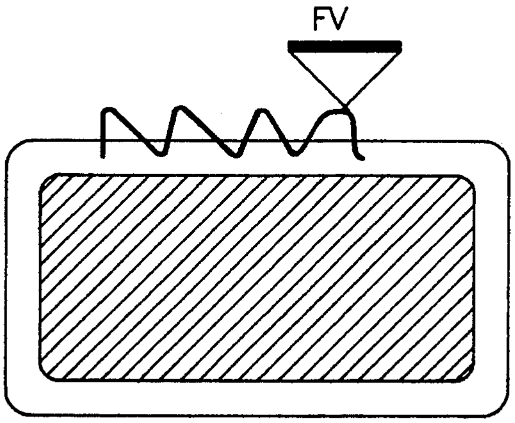
Figure 11C:
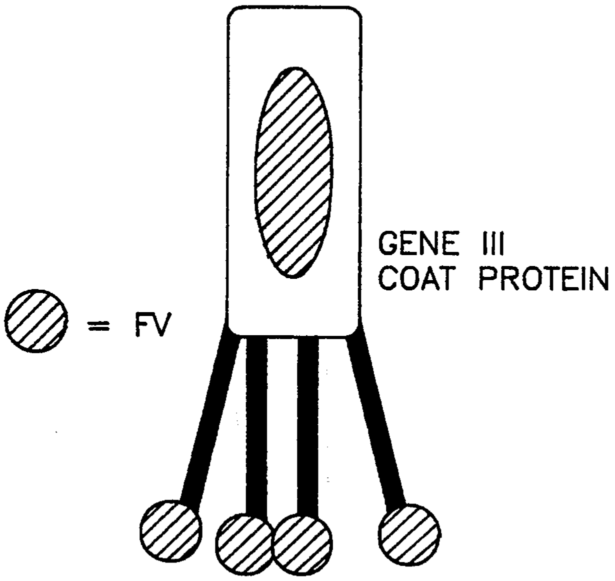
Figure 11D:
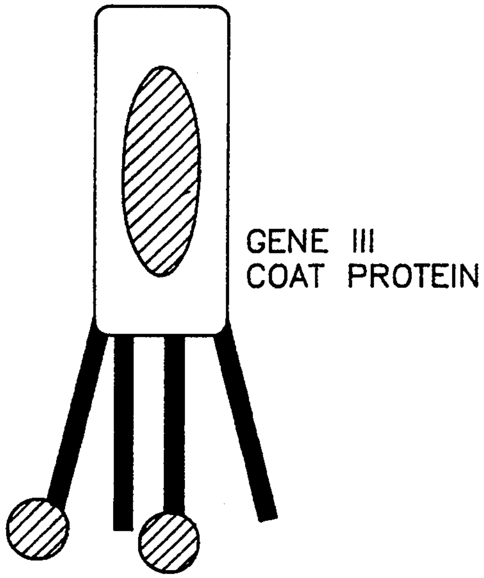

FIG. 10. Diagram of fusion proteins displayed by phagemid and helper phage.

FIGS. 11A–11D. Diagram of microorganisms displaying Fv antibodies. 11A: Phage antibody library, 11B: Iam B antibody fusion library, 11C: Phage antibody library, 11D: Phagemid antibody library.

Figure 12A:
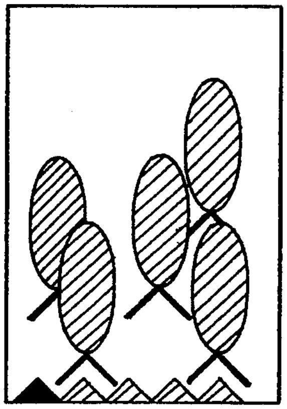
Figure 12B:
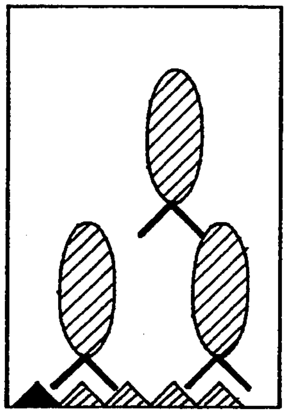
Figure 12C:
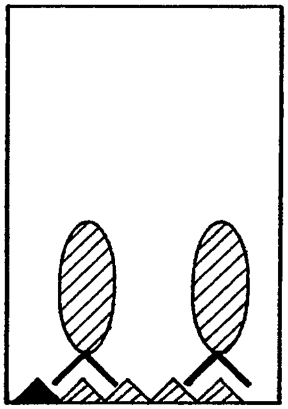

FIGS. 12A–12C. Antibody screening protocol 12A: step 1, 12B: step 2, 12C: step 3.

FIG. 13. Amino acid sequence of anti-tat Fv compared with sequence of FIG. 2 [SEQ ID:11].

FIG. 14. Nucleotide sequence of anti-tat Fv compared with sequence of FIG. 3 [SEQ ID:12].

DETAILED DESCRIPTION OF THE INVENTION

This invention is directed to a method for producing a protein corresponding to an antibody capable of binding to an antigen. This method involves synthesizing a plurality of synthetic genes, each of which contains both a predetermined nucleotide region encoding the framework regions of portions of the heavy chain and light chain of an antibody and undetermined nucleotide regions which contain a random sequence of nucleotides. The proteins encoded by the synthetic genes are expressed by inserting vectors containing the synthetic genes into microorganisms and allowing expression to occur. The expressed proteins are screened by using the antigen to obtain the protein which is capable of binding to the antigen. In one variant of this method, an undetermined nucleotide region may correspond in length to a nucleotide sequence which encodes a hypervariable region of an antibody to which the protein may correspond.

Synthetic genes, which are double-stranded oligonucleotides, may be assembled by any conventional method. DNA synthesis or recombinant techniques, or polymerase chain reaction or any combination of such techniques are contemplated. [SEQ ID:3], [SEQ ID:4], [SEQ ID:5], [SEQ ID:6], [SEQ ID:7], [SEQ ID:8], [SEQ ID:9], [SEQ ID:10]

A synthetic gene may be synthesized by providing plurality of oligonucleotides, each of which contains a portion of the synthetic gene. All the oligonucleotides when combined together form the entire nucleotide sequence of the synthetic gene, e.g., the predetermined and undetermined regions. The sequence of the oligonucleotides in combination is considered to include the sequence of either strand of the synthetic gene, which is double-stranded. For example, both the sequence of the coding strand and the sequence complementary thereto are included. The oligonucleotides themselves are synthesized by stepwise addition of nucleotides with the undetermined nucleotide regions that contain a random sequence of nucleotides being synthesized by stepwise addition of one nucleotide out of a mixture of nucleotides. A mixture of oligonucleotides may contain any two or more of the nucleotide bases adenine, guanine, cytosine, and thymine. Also included may be modified bases such as inosine. The mixture may be an equal mixture of any 2 or more bases or the mixture may contain predetermined fractions of any 2 or more bases, or the mixture may be completely random. The bases are commercially available from biological supply houses. Synthesis as described above may be accomplished by attachment of bases to a solid substrate and sequential addition of an individual base from a vessel containing such base, or of an unknown base from a vessel containing the mixture described. This may be done by machine as described in the Examples. The synthetic gene is then synthesized by annealing and extending the plurality of oligonucleotides. Polymerase chain reaction is one method for producing synthetic genes. Any method of assembling the synthesized oligonucleotides to create either strand of the synthetic gene may be used. Polymerase chain reaction (PCR) is an example. PCR techniques are well known in the art and described in the Examples. In a preferred approach, the oligonucleotides are used as PCR primers to obtain a single-stranded template for the synthetic gene. Each oligonucleotide containing portions of the predetermined and undetermined regions of the synthetic gene, as described above. In addition, each oligonucleotide contains at its 5′ and 3′ ends a nucleotide sequence of about 20 bases which sequence is complementary to about 20 bases of the sequence adjoining the given oligonucleotide's sequence on the synthetic gene. Under well-known conditions suitable for PCR, the set of oligonucleotides will anneal and extend to form a final product which is a single-stranded sequence forming one strand of the synthetic gene. This template can be used to form the synthetic gene by any conventional means. The complementary strand can be produced by adding a primer, bases, and a polymerase, for example. For much more efficient production, PCR can be used. Primers corresponding to either end of the synthetic gene can be artifically synthesized by any conventional means (most of the sequence of the synthetic gene is already known, as described, therefore the primer sequences are easily deduced). These primers are added to the synthetic gene template which was obtained as described above, under PCR conditions, which are well-known in the art. The final product of this reaction is multiple copies of the synthetic gene. This full approach as described may be used to form a plurality of synthetic genes, each gene containing a different undetermined region with a different specificity.

The vectors and microorganisms used to express the synthetic genes may be any conventional vectors and microorganisms. Examples are provided infra.

This invention also is drawn to a plurality of proteins, each protein being composed of predetermined framework regions of portions of the heavy and light chain of an antibody, which are linked to undetermined regions of the antibody, and which contain a random sequence of amino acids. The length of these undetermined regions may be any desired length. A preferred length is a length corresponding to that of a hypervariable region of an antibody. At least one of the proteins is capable of binding to an antigen for which an antibody is sought. The proteins may be single chain proteins or may be composed of more than one polypeptide chain. A specific example is a single chain polypeptide capable of binding to HIV-1 tat protein and which is composed of predetermined framework regions of portions of the heavy-chain and light-chain of an antibody, which are linked to undetermined regions which correspond in length to hypervariable regions of said antibody. The undetermined regions contain a sequence of amino acids capable of binding to HIV-1 tat protein. A preferred embodiment of this protein has the amino acid sequence of FIG. 13 [SEQ ID:11].

Part of the invention is a synthetic gene which encodes a single-chain polypeptide capable of binding to HIV-1 tat protein as described above. A particular example is the synthetic gene comprising the nucleotide sequence of FIG. 14 [SEQ ID:12].

The predetermined nucleotide regions of the synthetic gene encode selected regions of an antibody. Both the heavy and light chain subunits of an antibody are made up of conserved regions and variable regions, as is well known in the art. The variable regions themselves contain framework regions which themselves are relatively conserved, and complementary-determining (CDR) or hypervariable regions which are not conserved and which are specific to a given antibody. These regions determine binding specificity. The synthetic genes are designed to encode framework regions from both heavy and light chain variable regions, interspersed with undetermined regions containing random amino acid sequences. The undetermined regions may be of any length, and length may be selected to give desired effects. The length of the undetermined regions may correspond to the length of hypervariable regions of an antibody, such that the undetermined regions "fill in" for hypervariable regions and provide a randomized selection of possible binding specifications and affinities. The framework regions are derived from known antibodies. The boundaries of framework and hypervariable regions are well known in the art and one skilled in the art can determine the regions by conventional means. It is possible to obtain such antibodies from hybridomas, a variety of which are available commercially from depositories such as the ATCC or from biological supply houses. Hybridomas can also be produced by conventional methods. Or antibodies may be obtained from any cells which naturally express them or have gene inserts enabling their expression. Genes encoding antibodies may be obtained from any such sources and from cells which contain but do not express antibody genes. Actual antibodies or antibody genes may be used to make the synthetic genes with well known techniques of protein synthesis or genetic engineering. However, a preferred alternative is to obtain the known sequences of numerous specific antibodies from written publications or from a computer database such as those provided by Genbank or Brookhaven National Labs. A consensus framework sequence can then be generated based on these sequences. An example Of such a sequence is the sequence of FIG. 2 [SEQ ID:1]. The amino acids of the hypervariable regions have been replaced with "X" to represent any amino acid. This sequence may then be synthesized by conventional methods described above. Such a sequence obviates the need to use antibodies of animal origin and the limitations of such use, and the need to use cell cultures and cloning to obtain antibodies. Further, the consensus sequence can be biassed to favor expression in a selected microorganism, as described in the Examples. The synthetic genes may encode any antibodies or parts thereof. Preferred synthetic genes encode proteins which correspond to antibodies known in the art as Fv antibodies. These antibodies are composed of the variable regions (including hypervariable and framework) of the light and heavy chains of an antibody which are connected to each other by peptide bonds via a peptide linker sequence to form a single-chain polypeptide. Also preferred are synthetic genes encoding the antibodies known in the art as Fab fragments. These antibodies are also composed of the heavy and light chain variable regions, but form a double chain polypeptide wherein the heavy and light chain segments may be connected by disulfide bridges.

Part of this invention is a plurality of synthetic genes which encodes the plurality of proteins, each of which synthetic genes contains nucleotide sequences which encode predetermined framework regions of portions of the heavy chain and light chain of an antibody, which are linked to nucleotide sequences which encode undetermined regions containing a random sequence of amino acids. These regions may contain a number of nucleotides which encode a sequence corresponding in length to hypervariable regions of an antibody. At least one protein of the plurality of proteins is capable of binding to an antigen for which an antibody is desired. A particular example is a plurality of proteins wherein each of the proteins is a single-chain protein, or is composed of more than one chain.

Also contemplated in the invention is a vector having inserted therein a synthetic gene which contains nucleotide sequences encoding predetermined framework regions of portions of the heavy chain and light chain of an antibody, linked to nucleotide sequences which encode undetermined regions of any desired length, which also may correspond in length to hypervariable regions of an antibody, and containing a random sequence of amino acids. This vector is capable of causing expression of the synthetic gene as a protein by a microorganism. A preferred vector is one which can cause the expressed protein to translocate to the outer surface of the microorganism which contains the synthetic gene. Vectors include any conventional vectors. Vectors such as plasmids, cosmids, viruses, transposons, and any other elements capable of genetic transfer are Contemplated. The synthetic genes are inserted into the vectors by methods well known in the art of genetic engineering. Vectors capable of causing expression are intended to include all conventional genetic elements for inducing gene expression, e.g., start and stop codons, promotors, enhancers, etc. Vectors which can cause expression of a protein on the surface of a microorganism may include signal sequences which cause the protein to go through a cell membrane. Microorganism can be any cells into which vectors may be inserted. However, phages are herein also considered to be microorganisms. Display phages can be used into which genes may be inserted in such a position as to be expressed as a fusion protein with one of the phage's coat proteins on the phage's surface. Microorganisms may be bacteria, such as *E. coli*, yeast, fungi, algae, mammalian cells or any other prokaryotic or eukaryotic cell whether acellular or part of a tissue.

All vectors and microorganisms described are conventional and well-known in the art. Also conventional are techniques for inserting synthetic genes into vectors, and for inserting vectors into microorganisms. Transformation, transfection, electroporation, and protoplast fusion are examples of well-known methods.

Also part of this invention is a plurality of microorganisms, each of which has on its outer surface at least one protein of the plurality of proteins, each of the proteins being composed of predetermined framework regions of portions of the heavy-chain and light-chain of an antibody, which are linked to undetermined regions of any length, in particular corresponding length to hypervariable regions of the antibody and containing a random sequence of amino acids. Any conventional microorganism, such as a phage, may be used. Vectors such as those described above may be used to insert the synthetic genes which encode the proteins. The phages may themselves include such a synthetic gene. At least one of these proteins is capable of binding to an antigen for which an antibody is desired to be found. The plurality of microorganisms may be used as a screen to determine which of the proteins expressed by the microorganism that binds to a predetermined antigen. Any conventional screening method may be used. For example, the antigen may be fixed to a solid support such as a culture dish or a bead in a column. Medium containing the plurality of proteins expressed the surfaces of microorganisms is contacted with the support. The protein capable of binding to the antigen will bind to the immobilized antigen and thereby will itself be immobilized. Then, unbound protein is washed off. Next, the bound protein, still attached to the microorganism expressing it, is eluted from the antigen. Washing and elution conditons are well known in the art. The isolated microorganism contains the synthetic gene which encodes the protein which binds to the antigen. This synthetic gene can be used in conventional recombinant technology to produce the antigen binding protein in quantity and also in any desired modified forms. For example, the synthetic gene can be expressed in company with genes expressing constant regions of an antibody, under conditions known to cause aggregation of the protein with the constant regions to produce a complete antibody. Heavy chain constant regions of IgM, IgG, IgA, IgD, or IgE types could be used. Light chain constant regions of kappa or lambda types would also be used to combine with the protein.

Alternatively, the proteins themselves may be isolated from the microorganisms and used for screening by conventional means.

The Examples which follow further describe the invention and are not intended to limit the invention in any way.

EXAMPLES

Figure 1A:
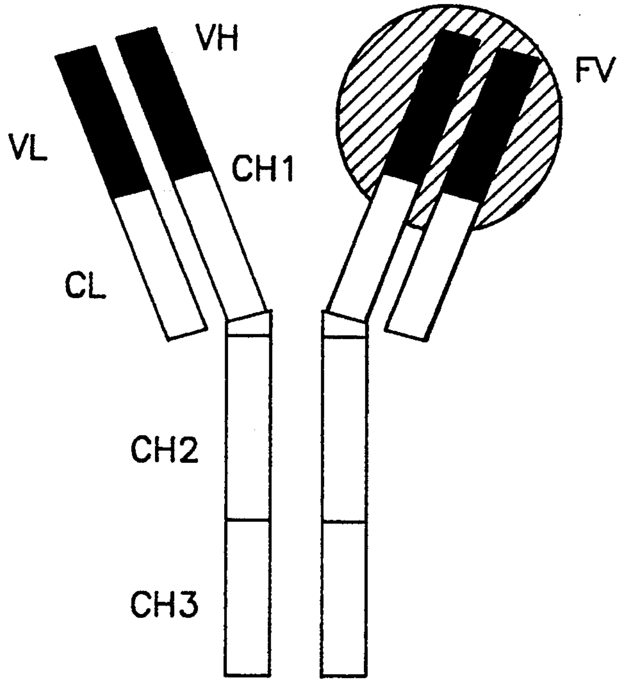
FIG. 1.
Figure 1B:
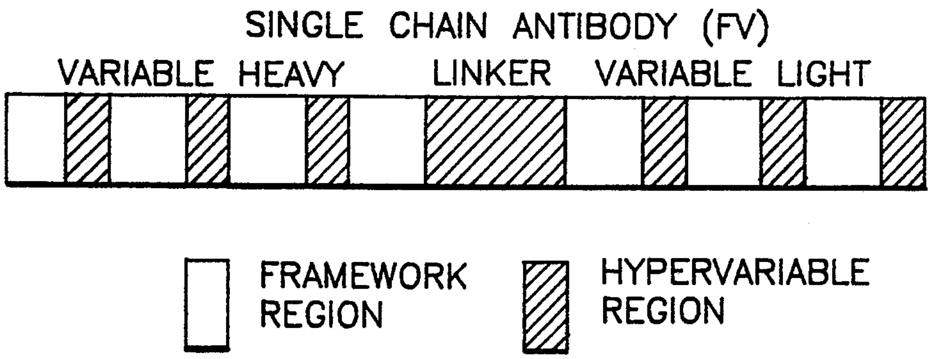
Figure 5A:
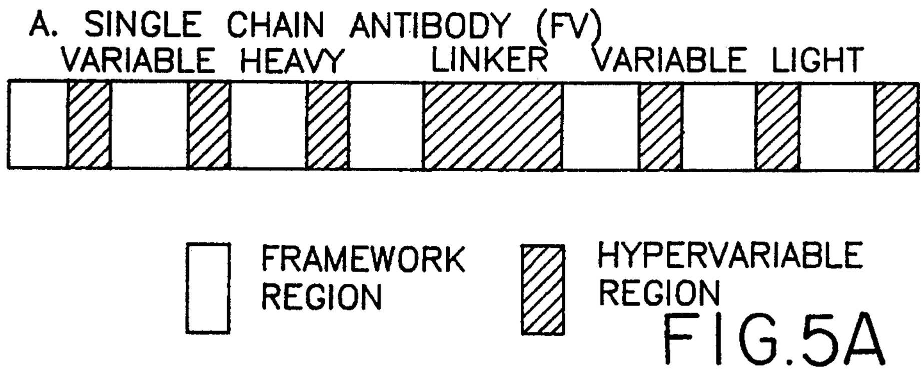
Figure 5B:
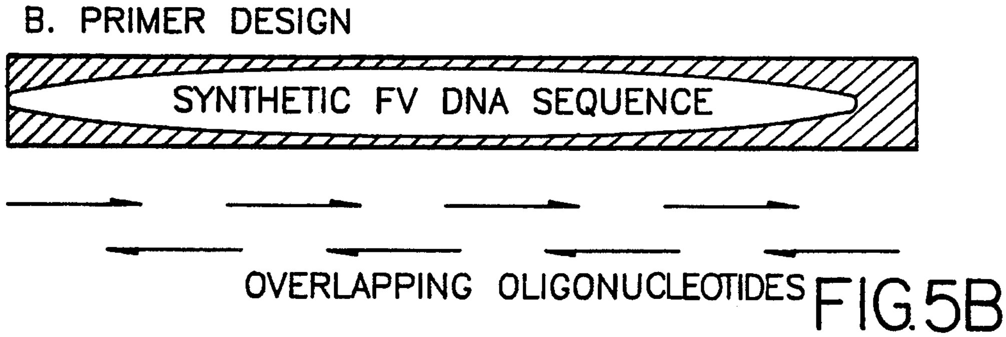
Figure 5C:
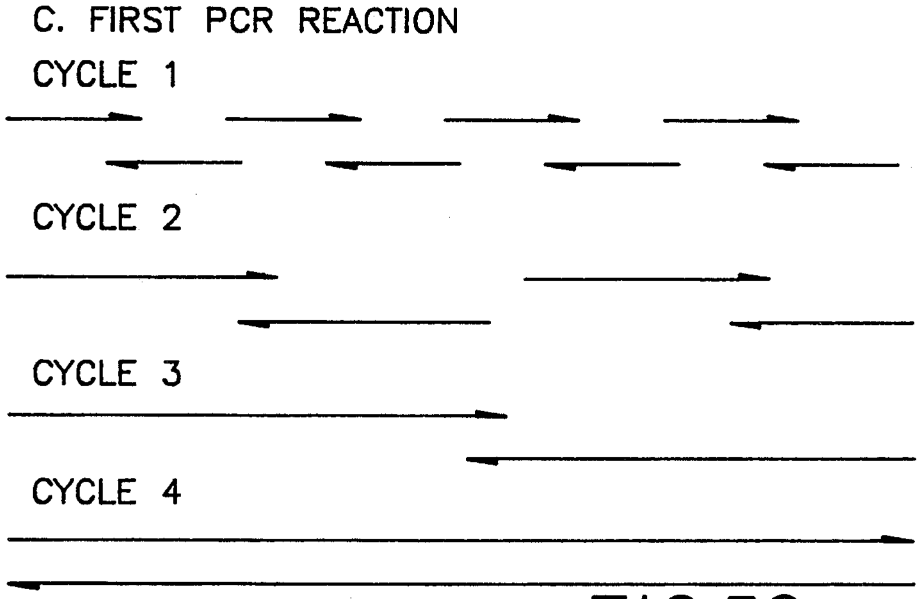
Figure 5D:
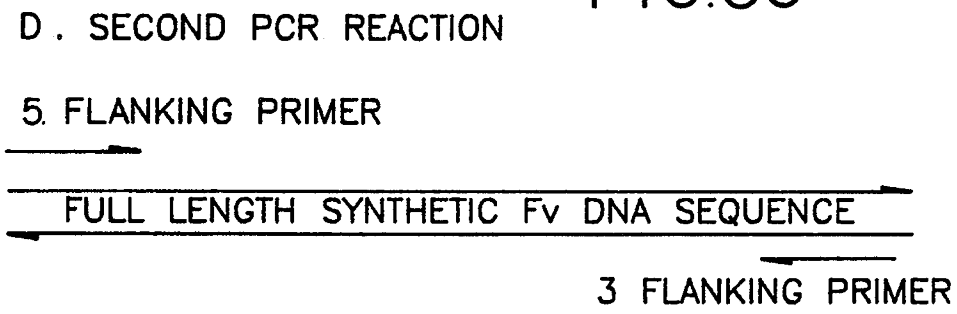

PCR is used to generate a library of completely de novo synthetic single chain antibodies (Fv) which consist of the heavy and light chain variable regions tethered together by a flexible glycine-serine linker (FIG. 1). Using a compilation of known human immunoglobulin amino acid sequences, a synthetic single chain Fv antibody fragment which contains conserved framework residues found in human antibodies and random residues in the hypervariable regions was designed. These artificial variable heavy and light chain domains are joined by a glycine-serine linker which for correct folding of the synthetic Fv fragment to allow formation of antigen binding sites. The synthetic Fv amino acid sequence was then reverse translated into a nucleic acid sequence with codon usage biased for expression in *E. coli*. The amino acids of the hypervariable regions were represented by degenerate triplets (NNN). The DNA encoding the synthetic Fv molecules was generated by a modification of the gene construction PCR method (Dillon, and Rosen, 1990). The resultant de novo synthesized Fv PCR products have been cloned into phage and phagemid display vectors or into bacterial outer membrane protein fusion expression vectors. In the phage display vector the single chain Fv is expressed as a fusion protein with the coat III protein of a M13 derivative single strand DNA bacteriophage (FUSE 5) (Parmley, and Smith, 1988). In the PAL (peptidoglycan associated lipoprotein) fusion vector, the Fv fragment should be expressed on the outer surface of the *E. coli* outer membrane as a fusion within the PAL protein (Fuchs et al. 1991; Chen, and Henning, 1987). Expression of the Fv fragments in phage or bacteria should allow for the rapid screening of the library by incubation of expressing phage or bacteria with immobilized antigen and sequential enrichment of specific antigen binding Fv expressing phage or bacteria. Since the DNA encoding the synthetic Fv will be present in the enriched phage or bacteria it is possible to sequence and subclone the single chain Fv fragments into additional antibody expression vectors.

These synthetic antibody libraries are screened with various antigens which have been immobilized on coated dishes, magnetic beads and affi-gel columns. The successful development and screening of these libraries allows the generation of novel antibody fragments, without the use of animals (or hybridoma technology), which recognize a wide variety of molecules including, non-immunogenic and tolerant epitopes, transcription factors, nuclear components, lipids, carbohydrates, etc. By virtue of the random amino acid sequence built into the hypervariable regions, the synthetic Fv library has the potential to bind almost any antigen regardless of its immunogenicity.

Design of synthetic single chain antibody sequence:

A compilation of known human antibody sequences was used to generate a consensus amino acid sequence of the variable regions for the light chain based on Kabat subgroup I and the heavy chain based on Kabat subgroup III (Kabat et al. 1987). Residues contained-within the hypervariable regions (CDRs) for the heavy and light chains were replaced with X amino acid, where X can represent any of the twenty amino acids. The redesigned heavy and light variable region sequences were then bridged by a flexible linker sequence encoded by the sequence GGGGSGGGGSGGGGS [SEQ ID:13]. The resulting synthetic antibody amino acid sequence shown in FIG. 2 [SEQ ID:1] was then reverse translated into a nucleic acid sequence in FIG. 3 [SEQ ID:2] with codon usage biased for expression in *E. coli* and for expression in *S. cerevisiae*. The degenerate X amino acid residues were encoded using degenerate codons of nnn where n represents any of the four nucleotides A,C,G or T.

PCR technique for generating DNA encoding synthetic single chain antibody sequence:

DNA encoding the synthetic antibody sequence was generated using an adaptation and modification of the method described by Dillon and Rosen (Dillon, and Rosen, 1990) for the PCR construction of synthetic genes and is outlined in FIG. 5. Briefly, eight long oligonucleotides were synthesized on an ABI oligonucleotide synthesizer which spanned the designed sequence of the synthetic antibody. These oligonucleotides were between 100 and 135 nucleotides in length and contained short overlaps approximately 20 nucleotides in length (FIG. 4). The overlaps were positioned such that they corresponded to defined sequences of the framework regions. Nucleotide positions designated by n were synthesized such that any of the four (A,C,G,T) phosphoramidites would be introduced to the solid support at the same time. This was accomplished by having the four phosphoramidites premixed in solution and placed in a separate reservoir which was utilized during synthesis for base positions designated n. Flanking primers were also synthesized which contained appropriate restriction sites to facilitate cloning.

Briefly, the two step PCR approach was used for generating the DNA fragment. The first PCR step was used to generate the full length templates and conditions were as follows 0.5 micrograms of each of the eight long overlapping oligonucleotides were mixed in a 100 microliter PCR reaction containing 2.5 units of AmpliTaq DNA polymerase and subjected to 35 cycles of thermal cycling in a Perkin-Elmer 9600 System thermal cycler. Cycle conditions were as follows: 5 minute initial denaturation at 94° C.; 15 seconds at 94° C., 15 seconds at 55° C., 45 seconds at 72° C. for 35 cycles, followed by a final extension at 72° C. for 3 minutes. A second PCR reaction was used to generate material for cloning. One to three microliters of the product from the first PCR reaction was used as template for a second reaction containing one microgram of each flanking primer and subjected to 25 cycles of thermal cycling as described above.

Vectors:

A phage display vector, FUSE 5 (FIG. 7) was obtained from George Smith (University of Missouri) and used for cloning the single chain antibody DNA in frame with the amino terminus of the gene III phage coat protein DNA at engineered SfiI sites (Parmley, and Smith, 1988).

The phagemid display vector BLSKDSgeneIII (FIG. 8) was constructed by ligating the lac promoter from the pDS56 vector (Bujard et al. 1987) as an XhoI-SphI fragment and a synthetic peIB leader sequence as a SphI-PstI fragment into the XhoI-PstI sites of Bluescript SK+ (Stratagene). The resultant plasmid, BLSKDSpeIB was further manipulated to include geneIII as an XbaI-NotI fragment which was obtained by PCR cloning from M13mp18.

The peptidoglycan associated lipoprotein (PAL) bacterial display vector BLSKDSPAL was constructed by PCR cloning of the PAL sequence (Chen, and Henning, 1987) from *E. coli* strain MC1061 using a 5′ primer which contained BamHI, NsiI, and XbaI sites and a 3′ primer which contained a NotI site. The PAL PCR product was then cloned as a BamHI-NotI fragment into BLSKDSpeIB.

Construction of *E. coli* helper phage strains:

PJD1 (FIG. 9): MC1061 was cotransformed with the lac repressor expression vector pDM1.1 (Bujard et al. 1987) and single strand DNA from the FUSE 2 phage (a tetracycline transducing phage obtained from George Smith) (Parmley, and Smith, 1988). The PJD1 strain is tetracycline and kanamycin resistant and can be made transformation competent for both heat shock and electroporation.

PJD2 (FIG. 9): Similar to PJD1 but lacks the pDM1.1 plasmid.

PJD3: MC1061 transformed by the interference resistant helper phage VCSM 13 (Stratgene). This strain is kanamycin resistant.

Construction of antibody phage libraries:

The synthetic single chain antibody PCR products were digested at their termini with SfiI and ligated into the SfiI sites of the FUSE5 phage display vector. Four micrograms of cut vector DNA was mixed with 0.5 micrograms of cut insert and ligated in a final volume of one milliliter with 5 units of T4 ligase and incubated at 16° C. for twelve hours. Ligations were then ethanol precipitated and resuspended in 10 microliters of water. The ligation mixture was then electroporated into electrocompetent MC1061 cells using a Biorad electroporator set at 2.5 kV, 400 ohms and 25 microfarads. The cells were then resuspended in 2 mL of SOC medium and incubated in Falcon 2071 polystyrene tube for one hour at 37° C. The transformed cells were then plated on LB agar plates containing 25 microgram per mL tetracycline and incubated overnight at 37° C. Tetracycline resistant colonies were then scraped from the plates into TBS and phage expressing the antibody were isolated and concentrated by PEG precipitation.

Construction of antibody phagemid libraries:

The synthetic single chain antibody PCR products were digested at their termini with NsiI and XbaI and ligated into the PstI and XbaI sites of the BLSKDSgeneIII display vector. Ligation mixtures were then electroporated into either electrocompetent *E. coli* strains PJD1, PJD2 or PJD3 which contain helper phage (as described). Transformed cells were the selected on LB agar containing ampicillin (100 ug/mL), tetracycline (25 ug/mL) and IPTG. Phage was then prepared by scraping colonies and treating as described above.

Construction of antibody PAL libraries:

The synthetic single chain antibody PCR products were digested at their termini with NsiI and XbaI and ligated into the NsiI and XbaI sites of the BLSKDSPAL display vector. Ligation mixes were electroporated as described above and transformed bacteria was grown on LB amp agar plates overnight. Colonies were then scraped and stored as glycerol stocks at −70° C. until use in screening.

Screening Protocols (FIG. 12)

Antigens used in screening were coupled to tosylactivated M-280 magnetic beads according to manufacturer's recommended conditions (Dynal). Antigens were also immobilized on Nunc 96 well micotiter plates or affigel resin for use in screening antibody phage (phagemids, or PAL fusion bacteria).

Screening using coated magnetic beads was carried out in siliconized microfuge tubes which had been preincubated with TBS plus 1% BSA for one hour at room temperature. For primary screenings, one uL of antigen coated beads were mixed with 5 uL of antibody phage preparations in a final volume of 1 mL of TBS plus 0.1% Tween-20 and 1% BSA. Incubations were carried out at 4° C. for one hour. The Phage bound magnetic beads were then concentrated using a MPC-6 (Dynal) magnetic particle concentrator and unbound phage was aspirated. The beads were then washed 10 to 20 times with TBS plus 0.1% Tween-20. This was done to wash away residual unbound and nonspecific phage. Phage which remained bound to the beads following the wash procedure were then eluted with either low pH, 0.2N HCl or by treatment with trypsin. In the case of low pH elution, the eluted phage were removed from the beads and neutralized with 2M Tris. The eluted phage were then used for infecting starved K91kan cells (a male *E. coli* strain obtained from George Smith) (Parmley, and Smith, 1988). The phage infected cells were selected for ampicillin (BLSKDS gene III phagemid Antibody library) or tetracycline (FUSE 5 Antibody library) transducing units. In the case of the phage library, antibody phage particles were prepared directly from the transduced colonies and used for sequential rounds of screening as described above. The phagemid library required the rescue procedure described next.

Rescue of phagemid:

Phagemid rescue procedures: Antibody phagemid infected K91kan cells were scraped from plates and grown in liquid culture for one hour at 37° C. at which time the culture was divided in half. One half was used for preparing phagemid DNA by the alkaline lysis procedure while the other half was used for rescue by use of either FUSE2 or VCSM 13 helper phage. The rescue was achieved by adding 108 helper phage to the K91kan cells and incubating for an additional hour at 37° C. After one hour the IPTG (final conc=1 mM) was added and in the case of FUSE2, tetracycline was also added. The culture was incubated for 4 to 8 hours at which time the culture supernatant was used to prepare packaged phagemid for sequential rounds of screening.

An alternative approach for phagemid rescue used transformation of the PJD1,2, and 3 strains by the isolated phagemid DNA. In this procedure, the transformed strains were selected with the appropriate antibiotics and rescued phagemid was prepared as described above and used in sequential screenings.

Results

The initial phage library constructed contained approximately $10^6$ to $10^7$ independent clones. This library was screened against magnetic beads coated with the HIV-1 tat protein. The result of one screening is shown as follows.

ANTIBODY PHAGE TR5 SCREEN

FIRST ROUND SCREEN

Input Phage=$10^{10}$. Phage particles from FUSE5 synthetic Fv library. Screened with 1 mircoliter of HIV-1 tat protein coated magnetic beads. Five tet$^r$ colonies were obtained.

SECOND ROUND SCREEN

Phage TR5 was grown and screened against tat and other protein coated beads.

| | PROTEIN | TAT | gp120 | P65 |
|---|---|---|---|---|
| Magnetic Bead | 1 | 277 | 1 | O |
| Volume | 5 | 1639 | 4 | ND |
| (microliters) | 10 | 4800 | 14 | ND |
| | Number of tet$^r$ colonies | | | |

One phage TR5 was identified which appeared to bind specifically to the Tat protein. In this experiment incubation of the purified phage with increasing amounts of tat coated beads resulted in an increase in the number of bound phage while little phage was observed to bind to increasing amounts of beads coated with other proteins. In addition, the TR5 phage was selected for in 4 separate screening experiments as determined by DNA sequencing of the phage insert of antibody phage which enriched against Tat protein.

Sequence comparison of the phage TR5 insert and the initial framework sequence designed showed few differences between the two as indicated in FIG. 14 [SEQ ID:12]. These changes did not significantly alter the amino acid sequence as compared in FIG. 13 [SEQ ID:11]. It is unclear if these alterations are a result of PCR amplification of the initial construct or subsequent PCR cloning steps or if they arose as a result of mutation in the phage genome. Characterization of the unscreened library indicated a selective pressure or stability constraints against some insert sequences as evidenced by observations of partial and entire deletions of the antibody insert.

Results from the phagemid library indicate that the insert is more readily maintained and that the cloning efficiency for construction of the library is much higher thereby making it possible to generate a larger and more diverse library. Our experiments show that it is possible to generate packaged phagemid by direct transformation into the PJD helper *E. coli* strains. Initial screening has shown that the same phagemid has been picked up 4 times and each of the 4 phage contain the same partial sequence.

The construction of a library composed of entirely synthetic antibodies has the potential to generate antibody molecules which have completely novel binding characteristics and the ability to bind virtually any antigen available for screening. Known human antibody sequences are used to form a consensus type framework sequence on which to base the design of an exemplary single chain antibody sequence. Following the design of the amino acid sequence of the synthetic antibody, the amino acid sequence was reverse translated into a nucleic acid sequence which contained codons that should be preferentially utilized in *E. coli.* This differs significantly from previously published antibody libraries which have all been derived from animal tissue (Garrard et al. 1991; Kang et al. 1991b; Kang et al. 1991a; Persson et al. 1991; Huse et al. 1989; Barbas III et al. 1991; Gussow et al. 1989; Clackson et al. 1991; McCafferty et al. 1990; Marks et al. 1991; Hoogenboom et al. 1991; Winter, and Milstein, 1991; Hodgson). The representation and expression of specific antibodies from these libraries may be hindered due to little or no expression of some library members as a result of poor codon usage in *E. coli.* The problems of codon usage in *E. coli* may be important for the generation of good libraries since phage (or phagemid) based vectors are being used for the display of the antibody molecules. Therefore, the inherent characteristic of the DNA encoding the synthetic antibody (SYNAB jargon term) may lead to increased expression of our antibody library.

The identification of the phage TR5 and its ability to bind the Tat protein confirm that functional synthetic antibodies have been generated based on a comparative analysis of known antibody sequences. This approach may be applied to the study of other proteins which belong to larger families such as the T cell receptors.

The use of phage display vectors offers many options for the screening of large antibody libraries. Screening conditions can be altered to select for various affinities. The use of gene III as a fusion for the single chain antibody allows expression of a limited number of molecules which may lower nonspecificity during screening. The use of trypsin for elution results in increased recovery of phage compared to low pH. The use of trypsin does not seem to interfere with the infectivity of the phage.

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 246 amino acids
( B ) TYPE: amino acid
( D ) TOPOLOGY: linear ( i i ) MOLECULE TYPE: protein ( x i ) SEQUENCE DESCRIPTION: SEQ ID NO:1:

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30

Xaa Xaa Xaa Trp Val Arg Gln Ala Pro Gly Lys Gly Leu Glu Trp Val
        35                  40                  45

Ala Xaa Xaa Xaa Xaa Xaa Xaa Xaa Xaa Xaa Xaa Xaa Xaa Xaa Xaa Xaa
    50                  55                  60

Xaa Xaa Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Xaa Xaa Xaa Xaa Xaa Xaa Xaa Xaa Xaa Xaa Xaa Xaa Xaa Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Xaa Xaa Xaa Xaa Xaa Xaa Xaa Xaa Xaa Xaa Xaa Trp Tyr Gln Gln Lys
                165                 170                 175

Pro Gly Lys Ala Pro Lys Leu Leu Ile Tyr Xaa Xaa Xaa Xaa Xaa Xaa
            180                 185                 190

Xaa Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Xaa Xaa Xaa Xaa Xaa Xaa Xaa Xaa Xaa Phe Gly Gln Gly Thr Lys
225                 230                 235                 240

Val Glu Ile Lys Arg Thr
                245
```

( 2 ) INFORMATION FOR SEQ ID NO:2:

-continued ( i ) SEQUENCE CHARACTERISTICS:
( A ) LENGTH: 738 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

```
GAAGTTCAAC TGGTTGAATC CGGTGGTGGT CTGGTTCAAC CAGGTGGTTC CCTGCGTCTG   60
TCCTGTGCTG CTTCCGGTTT CACCTTCTCC NNNNNNNNNN NNNNNTGGGT TCGTCAAGCT  120
CCAGGTAAAG GTCTGGAATG GGTTGCTNNN NNNNNNNNNN NNNNNNNNNN NNNNNNNNNN  180
NNNNNNNNNN NNNNNNNNCG TTTCACCATC TCCCGTGACG ACTCCAAAAA CACCCTGTAC  240
CTGCAAATGA ACTCCCTGCG TGCTGAAGAC ACCGCTGTTT ACTACTGTGC TCGTNNNNNN  300
NNNNNNNNNN NNNNNNNNNN NNNNNNNNNN NNNTGGGGTC AAGGTACCCT GGTTACCGTT  360
TCCTCCGGTG GTGGTGGTTC CGGTGGTGGT GGTTCTGGTG GTGGTGGTTC CGACATCCAA  420
ATGACCCAAT CCCCATCCTC TCTGTCCGCT TCCGTTGGTG ACCGTGTTAC CATCACCTGT  480
NNNNNNNNNN NNNNNNNNNN NNNNNNNNNN NNNTGGTACC AACAAAAACC AGGTAAAGCT  540
CCAAAACTGC TGATCTACNN NNNNNNNNNN NNNNNNNNNG GTGTTCCATC CCGTTTCTCC  600
GGTTCCGGTT CTGGTACCGA CTTCACCCTG ACCATCTCCT CTCTGCAACC AGAAGACTTC  660
GCTACCTACT ACTGTNNNNN NNNNNNNNNN NNNNNNNNNN NNTTCGGTCA AGGTACCAAA  720
GTTGAAATCA AACGTACC                                                738
```

( 2 ) INFORMATION FOR SEQ ID NO:3:

( i ) SEQUENCE CHARACTERISTICS:
( A ) LENGTH: 125 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

```
GAAGTTCAAC TGGTTGAATC CGGTGGTGGT CTGGTTCAAC CAGGTGGTTC CCTGCGTCTG   60
TCCTGTGCTG CTTCCGGTTT CACCTTCTCC NNNNNNNNNN NNNNNTGGGT TCGTCAAGCT  120
CCAGG                                                              125
```

( 2 ) INFORMATION FOR SEQ ID NO:4:

( i ) SEQUENCE CHARACTERISTICS:
( A ) LENGTH: 120 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:4:

```
GGAGTCGTCA CGGGAGATGG TGAAACGNNN NNNNNNNNNN NNNNNNNNNN NNNNNNNNNN   60
NNNNNNNNNN NNNNNNNNAG CAACCCATTC CAGACCTTTA CCTGGAGCTT GACGAACCCA  120
```

( 2 ) INFORMATION FOR SEQ ID NO:5:

( i ) SEQUENCE CHARACTERISTICS:
( A ) LENGTH: 96 base pairs
( B ) TYPE: nucleic acid
( C ) STRANDEDNESS: single
( D ) TOPOLOGY: linear ( i i ) MOLECULE TYPE: cDNA -continued ( x i ) SEQUENCE DESCRIPTION: SEQ ID NO:5:

CGTTTCACCA TCTCCCGTGA CGACTCCAAA AACACCCTGT ACCTGCAAAT GAACTCCCTG 60

CGTGCTGAAG ACACCGCTGT TTACTACTGT GCTCGT 96

( 2 ) INFORMATION FOR SEQ ID NO:6:

( i ) SEQUENCE CHARACTERISTICS:
( A ) LENGTH: 101 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

CACCGGAGGA AACGGTAACC AGGGTACCTT GACCCCANNN NNNNNNNNNN NNNNNNNNNN 60

NNNNNNNNNN NNNNNNACGA GCACAGTAGT AAACAGCGGT G 101

( 2 ) INFORMATION FOR SEQ ID NO:7:

( i ) SEQUENCE CHARACTERISTICS:
( A ) LENGTH: 126 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

TGGTTACCGT TTCCTCCGGT GGTGGTGGTT CCGGTGGTGG TGGTTCTGGT GGTGGTGGTT 60

CCGACATCCA AATGACCCAA TCCCCATCCT CTCTGTCCGC TTCCGTTGGT GACCGTGTTA 120

CCATCA 126

( 2 ) INFORMATION FOR SEQ ID NO:8:

( i ) SEQUENCE CHARACTERISTICS:
( A ) LENGTH: 106 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

GATCAGCAGT TTTGGAGCTT TACCTGGTTT TTGTTGGTAC CANNNNNNNN NNNNNNNNNN 60

NNNNNNNNNN NNNNNACAGG TGATGGTAAC ACGGTCACCA ACGGAA 106

( 2 ) INFORMATION FOR SEQ ID NO:9:

( i ) SEQUENCE CHARACTERISTICS:
( A ) LENGTH: 119 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:9:

GGTACGTTTG ATTTCAACTT TGGTACCTTG ACCGAANNNN NNNNNNNNNN NNNNNNNNNN 60

NNNACAGTAG TAGGTAGCGA AGTCTTCTGG TTGCAGAGAG GAGATGGTCA GGGTGAAGT 119

( 2 ) INFORMATION FOR SEQ ID NO:10:

( i ) SEQUENCE CHARACTERISTICS:
( A ) LENGTH: 116 base pairs

-continued ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:10:

CAGGTAAAGC TCCAAAACTG CTGATCTACN NNNNNNNNNN NNNNNNNNNN GGTGTTCCAT 60

CCCGTTTCTC CGGTTCCGGT TCTGGTACCG ACTTCACCCT GACCATCTCC TCTCTG 116

( 2 ) INFORMATION FOR SEQ ID NO:11:

( i ) SEQUENCE CHARACTERISTICS:
( A ) LENGTH: 246 amino acids
( B ) TYPE: amino acid
( D ) TOPOLOGY: linear ( i i ) MOLECULE TYPE: protein ( x i ) SEQUENCE DESCRIPTION: SEQ ID NO:11:

Glu Val Gln Leu Val Glu Ser Gly Arg Gly Leu Val Gln Pro Gly Gly
1 5 10 15

Ser Leu Arg Leu Ser Cys Ala Ala Ser Gly Phe Thr Phe Ser His Phe
20 25 30

Leu Val Ala Trp Val Arg Gln Ala Pro Gly Lys Gly Leu Glu Trp Val
35 40 45

Ala Thr Tyr Ser Met Ile Ser Arg Ala Arg Val Leu Asp Gly Ser Phe
50 55 60

Asn Gly Arg Tyr Thr Ile Ser Arg Asp Asp Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ile Gly Ser Thr His Thr Ile Pro Arg Leu Ser Gln Tyr Gly
100 105 110

Gly Gln Gly Thr Leu Val Thr Val Ser Ser Gly Gly Gly Gly Ser Gly
115 120 125

Gly Gly Gly Ser Gly Gly Gly Gly Ser Asp Ile Gln Met Thr Gln Ser
130 135 140

Pro Ser Ser Leu Ser Ala Ser Val Gly Asp Arg Val Thr Ile Thr Cys
145 150 155 160

Lys Leu Arg Gly Pro Gln Pro His Ala Ile Thr Trp Tyr Gln Gln Lys
165 170 175

Pro Gly Lys Ala Pro Lys Leu Leu Ile Tyr Tyr Asp Gly Gln Thr Leu
180 185 190

Val Gly Val Pro Ser Arg Phe Ser Gly Ser Gly Ser Gly Thr Asp Phe
195 200 205

Thr Pro Thr Ile Ser Ser Leu Glu Pro Glu Asp Phe Ala Thr Tyr Tyr
210 215 220

Cys Thr Pro Thr His Lys Ile Asp Ser Pro Phe Gly Gln Gly Thr Lys
225 230 235 240

Val Glu Ile Lys Arg Thr
245

( 2 ) INFORMATION FOR SEQ ID NO:12:

( i ) SEQUENCE CHARACTERISTICS:
( A ) LENGTH: 738 base pairs
( B ) TYPE: nucleic acid
( C ) STRANDEDNESS: single
( D ) TOPOLOGY: linear ( i i ) MOLECULE TYPE: cDNA -continued ( x i ) SEQUENCE DESCRIPTION: SEQ ID NO:12:

```
GAAGTTCAAC TGGTTGAATC CGGTCGTGGT CTGGTTCAAC CAGGTGGTTC CCTGCGTCTG    60
TCCTGTGCTG CTTCCGGTTT CACCTTCTCC CATTTTTTGG TGGCGTGGGT TCGTCAAGCT   120
CCAGGTAAAG GTCTGGAATG GGTTGCTACC TACTCAATGA TTAGCCGGGC CCGAGTACTC   180
GATGGCTCCT TTAATGGACG TTACACCATC TCCCGTGACG ACTCCAAAAA CACCCTGTAC   240
CTGCAAATGA ACTCCCTGCG TGCTGAAGAC ACCGCTGTTT ACTACTGTGC TCGTATTGGT   300
TCTACGCACA CAATCCCACG ACTGTCTCAA TACGGGGGTC AAGGTACCCT GGTTACCGTT   360
TCCTCCGGTG GTGGTGGTTC CGGTGGTGGT GGTTCTGGTG GTGGTGGTTC CGACATCCAA   420
ATGACCCAAT CCCCATCCTC TCTGTCCGCT TCCGTTGGTG ACCGTGTTAC CATCACCTGT   480
AAACTCAGAG GACCACAACC ACACGCCATT ACATGGTACC AACAAAAACC AGGTAAAGCT   540
CCAAAACTGC TGATCTACTA CGACGGCCAA ACGTTGGTGG GTGTTCCATC CCGTTTCTCC   600
GGTTCTGGTT CTGGTACCGA CTTCACCCCG ACCATCTCCT CTCTGGAACC AGAAGACTTC   660
GCTACCTACT ACTGTACTCC TACGCACAAG ATCGATAGCC CATTCGGTCA AGGTACCAAA   720
GTTGAAATCA AACGTACC                                                 738
```

( 2 ) INFORMATION FOR SEQ ID NO:13:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( x i ) SEQUENCE DESCRIPTION: SEQ ID NO:13:

```
Gly Gly Gly Gly Ser Gly Gly Gly Gly Ser Gly Gly Gly Gly Ser
1               5                   10                  15
```

REFERENCES

Barbas III, C., Kang, A., Lerner, R., and Benkovic, S. (1991). Assembly of combinatorial antibody libraries on phage surfaces: The gene III site. Proc. Natl. Acad. Sci. USA 88, 7978–7982.

Bujard, H., Gentz, R., Lanzer, M., Stueber, D., Mueller, M., Imbrahimi, I., Haeuptley, M. T., and Dobberstein, B. (1987). A T5 promoter-based transcription-translation system for the analysis of proteins in vitro and in vivo. In Methods in Enzymology, R. Wu, ed. (San Diego: Academic Press), pp. 416–433.

Chen, R., and Henning, U. (1987). Nucleotide sequence of the gene for the peptidoglycan-associated lipoprotein of *Escherichia coli* K12. European Journal of Biochemistry 163, 73–77.

Clackson, T., Hoogenboom, H., Griffiths, A., and Winter, G. (1991). Making antibody fragments using phage display libraries. Nature 352, 624–628.

Co, M. S., and Queen, C. (1991). Humanized antibodies for therapy. Nature 51, 501–502.

Dillon, P. J., and Rosen, C. A. (1990). A rapid method for the construction of synthetic genes by the polymerase chain reaction. BioTechniques 9, 298–300.

Duschosal, M., Eming, S., Fischer, P., Leturcq, D., Barbas III, C., McConahey, P., Caothein, R., Thornton, G., Dixon, F., and Burton, D. (1992). Immunization of hu-PBL-SCID mice and the rescue of human monoclonal Fab fragments through combinatorial libraries. Nature 355, 258–262.

Fuchs, P., Breitling, F., Dubel, S., Seehaus, T., and Little, M. (1991). Targeting recombinant antibodies to the surface of *Escherichia coli*: Fusion to a peptidoglycan associated lipoprotein. Bio/Technology 9, 1369–1372.

Garrard, L., Yang, M., O'Connell, M., Kelley, R., and Henner, D. (1991). Fab assembly and enrichment in a monovalent phage display system. Bio/Technology 9, 1373–1377.

Gussow, D., Ward, E. S., Griffiths, A. D., Jones, P. T., and Winter, G. (1989). Generating binding activities from *Escherichia coli* by expression of a repertoire of immunoglobulin variable domains. Cold Spring Harbor Laboratory Press, NY Quantitative Biol., Hodgson, J. (1991). Making monoclonals in microbes. Bio/Technology 9, 421–425.

Hoogenboom, H., Griffiths, A., Johnson, K., Chiswell, D., Hudson, P., and Winter, G. (1991). Multi-subunit proteins on the surface of filamentous phage: methodologies for displaying antibody (Fab) heavy and light chains. Nucleic Acids Res. 19, 4133–1437.

Huse, W., Sastry, L., Iverson, S., Kang, A., Alting-Mees, M., Burton, D., Benkovic, S., and Lerner, R. (1989). Generation of a large combinatorial library of the immunoglobulin repertoire in phage lambda. Science 246, 1275–1281.

Kabat, E., Wu, T., Reid-Miller, M., Perry, H., and Gottesman, K. (1987). Sequences of Proteins of Immunological Interest 4th Edition, Kang, A., Barbas, C., Janda, K., Benkovic, S., and Lerner, R. (1991a). Linkage of recognition and replication functions by assembling combinatorial antibody Fab libraries along phage surfaces. Proc. Natl. Acad. Sci. USA 88, 4363–4366.

Kang, A., Jones, T., and Burton, D. (1991b). Antibody redesign by chain shuffling from random combinatorial immunoglobulin libraries. Proc. Natl. Acad. Sci. USA 88, 11120–11123.

Marks, J., Hoogenboom, H., Bonnert, T., McCafferty, J., Griffiths, A., and Winter, G. (1991). By-passing immunization: Human antibodies from V-gene libraries displayed on phage. J. Mol. Biol. 222, 581–597.

McCafferty, J., Griffiths, A., Winter, G., and Chiswell, D. (1990). Phage antibodies: Filamentous phage displaying antibody variable domains. Nature 348, 552–554.

Orlandi, R., Gussow, D., Jones, P., and Winter, G. (1989). Cloning immunoglobulin variable domains for expression by the polymerase chain reaction. Proc. Natl. Acad. Sci. USA 86, 3833–3837.

Parmley, S. F., and Smith, G. P. (1988). Antibody-selectable filamentous fd phage vectors: affinity purification of target genes. Gene 73, 305–318.

Persson, M., Caothien, R., and Burton, D. (1991). Generation of diverse high-affinity human monoclonal antibodies by repertoire cloning. Proc. Natl. Acad. Sci. USA 88, 2432–2436.

Winter, G., and Milstein, C. (1991). Man-made antibodies. Nature 349, 293–299.

We claim:

1. A method for producing a synthetic antibody that binds to an antigen, comprising:

a. constructing a plurality of synthetic genes, each of said synthetic genes comprising a predetermined nucleotide region encoding the framework regions of portions of the heavy chain of an antibody, another predetermined nucleotide region encoding the framework regions of portions of the light chain of an antibody, and an undetermined nucleotide region which contains a random sequence of nucleotides, said undetermined nucleotide region being synthesized by stepwise addition of nucleotides selected at random from a mixture of nucleotides;

b. expressing a plurality of proteins encoded by the plurality of synthetic genes from step (a), in microorganisms having inserted therein vectors comprising said synthetic genes; and c. contacting said plurality of proteins with the antigen to obtain said synthetic antibody binding to the antigen.

2. The method of claim 1 wherein said undetermined nucleotide region corresponds in length to a nucleotide sequence which encodes a hypervariable region of the antibody to which the protein corresponds.

3. The method of claim 1 wherein the synthetic gene included within said plurality of synthetic genes is synthesized by providing a plurality of oligonucleotides each of which contains a portion of the nucleotide sequence of a synthetic gene, the plurality of oligonucleotides being constructed such that all of said oligonucleotides combined together form the entire undetermined and determined nucleotide region sequence of said synthetic gene or a sequence complementary thereto, said oligonucleotides being synthesized by the stepwise addition of nucleotides, with the undetermined nucleotide regions which contain a random sequence of nucleotides being synthesized by the stepwise addition of one nucleotide from a mixture of nucleotides, and said synthetic gene being synthesized by annealing and extending said .plurality of oligonucleotides to form said synthetic gene.

4. The method of claim 3 wherein the predetermined nucleotide regions of said oligonucleotides are synthesized stepwise by adding one of the individual nucleotides adenine, cytosine, guanine, or thymine and the undetermined nucleotide regions of said oligonucleotides are synthesized stepwise by addition of any one of said nucleotides from a mixture.

5. The method of claim 3 wherein the plurality of oligonucleotides are annealed and extended by a polymerase chain reaction.

6. The method of claim 1 wherein the vectors containing said synthetic genes are display vectors.

7. The method of claim 4 wherein the undetermined nucleotide regions correspond in length to a nucleotide region which encodes the hypervariable regions of the antibody.

8. The method of claim 6 wherein said plurality of proteins expressed by the microorganisms are located at the surface of said microorganisms through the use of said display vector, contacting said plurality of proteins for binding to said antigen, being carried out while said plurality of proteins are located at the surface of said microorganisms.

* * * * *